US012127836B2

(12) United States Patent
Torris et al.

(10) Patent No.: US 12,127,836 B2
(45) Date of Patent: Oct. 29, 2024

(54) CLOSURE FOR A BIOLOGICAL FLUID COLLECTION DEVICE

(71) Applicant: Becton, Dickinson and Company, Franklin Lakes, NJ (US)

(72) Inventors: Anthony V. Torris, Montclair, NJ (US); Jamieson W. Crawford, Hagersten (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 874 days.

(21) Appl. No.: 17/051,533

(22) PCT Filed: May 2, 2019

(86) PCT No.: PCT/US2019/030403
§ 371 (c)(1),
(2) Date: Oct. 29, 2020

(87) PCT Pub. No.: WO2019/213397
PCT Pub. Date: Nov. 7, 2019

(65) Prior Publication Data
US 2021/0228123 A1    Jul. 29, 2021

Related U.S. Application Data

(60) Provisional application No. 62/666,765, filed on May 4, 2018.

(51) Int. Cl.
*A61B 5/15*      (2006.01)
(52) U.S. Cl.
CPC .. *A61B 5/150351* (2013.01); *A61B 5/150343* (2013.01); *A61B 5/150992* (2013.01)

(58) Field of Classification Search
CPC ........ A61B 5/150351; A61B 5/150343; A61B 5/150992; A61B 5/150366; A61B 5/153; (Continued)

(56) References Cited

U.S. PATENT DOCUMENTS 3,017,050 A * 1/1962 Barr, Sr. ............. B01L 3/50825
                                                        D24/224
4,942,966 A * 7/1990 Kemp ................... B01L 3/5082
                                                        206/521

(Continued)

FOREIGN PATENT DOCUMENTS

EP      1767935 A1    3/2007
EP      2702943 A1 *  3/2014    ........... A61B 5/1405
(Continued)

*Primary Examiner* — Yi-Shan Yang
*Assistant Examiner* — Jonathan E. Cooper
(74) *Attorney, Agent, or Firm* — The Webb Law Firm

(57) ABSTRACT

A closure for protectively sealing a biological fluid collection device is disclosed. The closure includes a cap and an adapter or connector. The closure of the present disclosure allows for connection to multiple different blood collection devices. In a first configuration, with the cap connected to the adapter, the closure may be connected to a first blood collection device. In a second configuration, with the cap disconnected from the adapter, the closure may be connected to a second blood collection device. An advantage of the closure of the present disclosure is that it enables a single closure device to accommodate a variety of connection options, hi one embodiment, the closure includes a barrier in communication with a portion of the cap, and the barrier protectively shields a portion of the stopper and/or protectively shields a portion of the cap.

18 Claims, 16 Drawing Sheets

(58) Field of Classification Search
CPC ......... B01L 2200/023; B01L 2200/025; B01L 2200/026; B01L 2200/0615; B01L 2200/0689; B01L 2200/085; B01L 2300/042; B01L 2300/044; B01L 3/523; B01L 3/50825; B01L 3/565; B01L 3/502
USPC ...................................................... 600/573
See application file for complete search history.

(56) References Cited

U.S. PATENT DOCUMENTS

| | | | |
|---|---|---|---|
| 5,511,558 A | 4/1996 | Shepard et al. | |
| 6,361,505 B1 | 3/2002 | Rainen et al. | |
| 2003/0153895 A1* | 8/2003 | Leinsing | B01L 3/50825 604/403 |
| 2005/0065454 A1 | 3/2005 | Manoussakis | |
| 2005/0267384 A1 | 12/2005 | Sauer et al. | |
| 2009/0259145 A1 | 10/2009 | Bartfeld et al. | |
| 2010/0055698 A1 | 3/2010 | Stibelli et al. | |
| 2011/0091990 A1 | 4/2011 | Dastane et al. | |
| 2014/0305196 A1* | 10/2014 | Ellis | G01N 1/34 210/321.72 |
| 2014/0308164 A1* | 10/2014 | Wilkinson | A61B 5/150748 422/514 |
| 2014/0322104 A1* | 10/2014 | Philipak | B29C 45/44 264/318 |
| 2015/0224497 A1 | 8/2015 | Furrer et al. | |
| 2015/0290640 A1* | 10/2015 | Goettke | B01L 3/5021 220/288 |
| 2016/0100784 A1* | 4/2016 | Kashmirian | A61B 5/150351 600/573 |
| 2016/0367177 A1 | 12/2016 | Edelhauser et al. | |
| 2017/0128934 A1* | 5/2017 | Kushon | A61B 5/150343 |

FOREIGN PATENT DOCUMENTS

| | | |
|---|---|---|
| JP | S63178956 A | 7/1988 |
| JP | 200595621 A | 4/2005 |
| WO | 2016205779 A2 | 12/2016 |
| WO | 2018226994 A1 | 12/2018 |
| WO | 2019156932 A1 | 8/2019 |

* cited by examiner

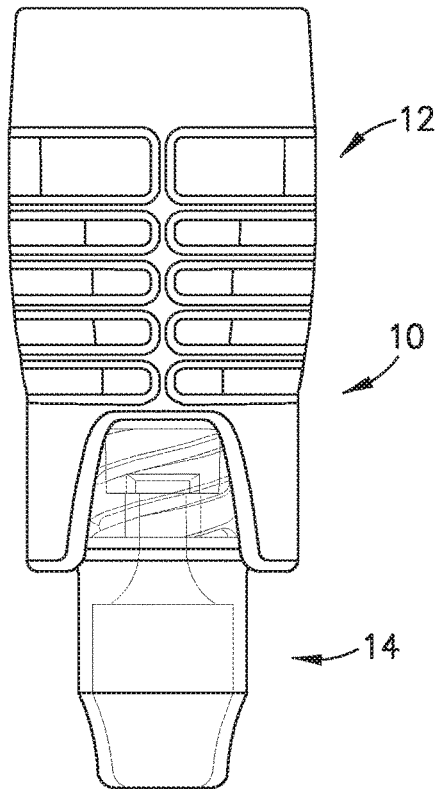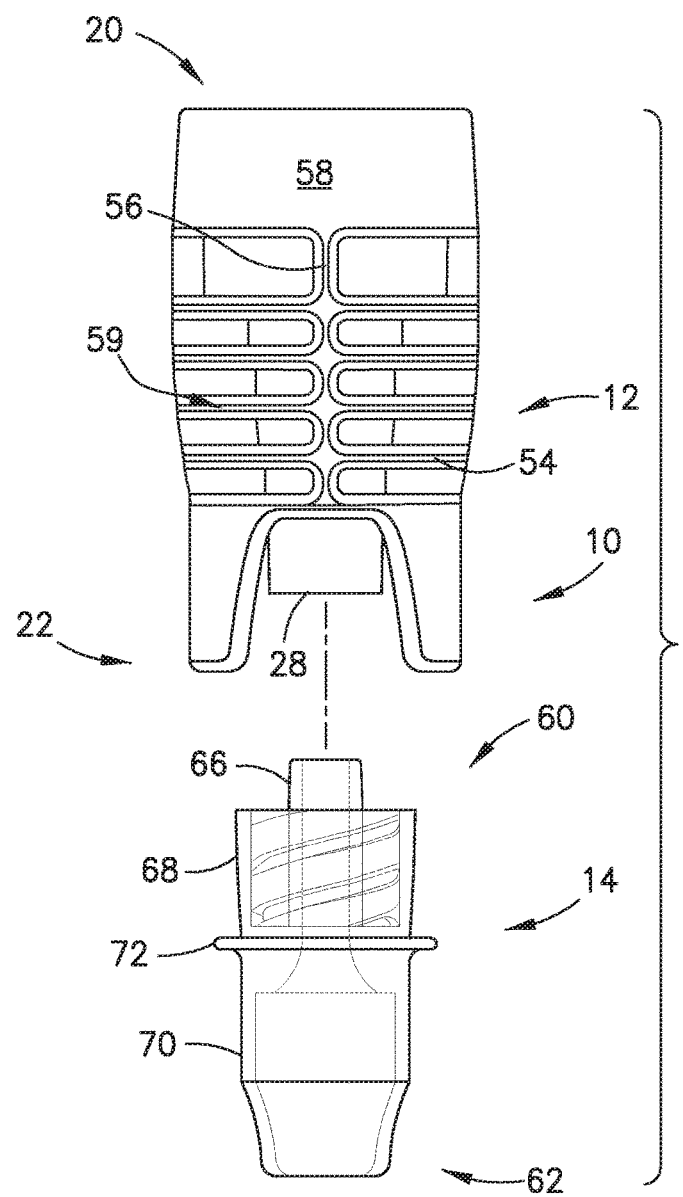
FIG.2
FIG.3

CLOSURE FOR A BIOLOGICAL FLUID COLLECTION DEVICE

CROSS-REFERENCE TO RELATED APPLICATIONS

This application is the United States national phase of International Application No. PCT/US2019/030403 filed May 2, 2019, and claims priority to U.S. Provisional Application Ser. No. 62/666,765 entitled "Closure for a Biological Fluid Collection Device", and filed May 4, 2018, the entire disclosures of which are incorporated by reference in their entirety.

BACKGROUND OF THE INVENTION

Field of the Disclosure

The present disclosure relates generally to biological fluid collection devices. More particularly, the present disclosure relates to a closure for a biological fluid collection device that seals a blood collection device and provides protection from a blood sample contacting a healthcare practitioner.

Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, and coagulation, for example.

It is important that blood collection devices are properly sealed to prevent unwanted spillage of a portion of a blood sample. Also, during a blood collection procedure, unwanted blood splattering may occur. Such blood splattering may cause a portion of a blood sample to contact a healthcare practitioner. Accordingly, there is a need for a closure for a blood collection device that protectively seals the blood collection device and that provides protection from a blood sample contacting a healthcare practitioner.

SUMMARY OF THE INVENTION

The present disclosure provides a closure for protectively sealing a biological fluid collection device. The closure includes a cap and an adapter or connector. The closure of the present disclosure allows for connection to multiple different blood collection devices. In a first configuration, with the cap connected to the adapter, the closure may be connected to a first blood collection device. In a second configuration, with the cap disconnected from the adapter, the closure may be connected to a second blood collection device. An advantage of the closure of the present disclosure is that it enables a single closure device to accommodate a variety of connection options. In one embodiment, the closure includes a barrier in communication with a portion of the cap, and the barrier protectively shields a portion of the stopper and/or protectively shields a portion of the cap.

In accordance with an embodiment of the present invention, a closure for a biological fluid collection device includes a cap having a first cap end, a second cap end, and defining a cap channel therein, the cap having a pierceable self-sealing stopper within a portion of the cap channel and a cap connection portion at the second cap end; and an adapter having a first adapter end, a second adapter end, and defining an adapter channel therein, the adapter having an adapter connection portion at the first adapter end, the cap connection portion removably connectable with the adapter connection portion, wherein, with the cap connected to the adapter, the closure is connectable to a first blood collection device via the cap, and wherein, with the cap disconnected from the adapter, the closure is connectable to a second blood collection device via the first adapter end of the adapter.

In one configuration, the cap defines a first cap channel portion therein having a first diameter, and a second cap channel portion therein having a second diameter, wherein the first diameter is greater than the second diameter. In another configuration, the stopper has a top portion and a bottom portion, the stopper contained within the cap channel such that the top portion of the stopper is within the first cap channel portion and the bottom portion of the stopper is within the second cap channel portion. In yet another configuration, the stopper defines a shoulder portion between the top portion and the bottom portion and the cap defines a ledge portion between the first cap channel portion and the second cap channel portion, wherein the stopper is contained within the cap channel such that the shoulder portion of the stopper contacts the ledge portion of the cap. In one configuration, the closure is connectable to a blood collection tube via the second adapter end of the adapter. In another configuration, with the closure connected to the blood collection tube, the closure seals the blood collection tube. In yet another configuration, the first blood collection device is a tube holder. In one configuration, the second blood collection device is a line. In another configuration, the cap connection portion comprises a first Luer connection portion and the adapter connection portion comprises a second Luer connection portion for mating connection with the first Luer connection portion. In yet another configuration, the first cap end includes a first wall shield portion that protectively shields the stopper, and the second cap end includes a second wall shield portion that protectively shields the first adapter end. In one configuration, with the cap connected to the adapter, the cap channel is in fluid communication with the adapter channel.

In accordance with another embodiment of the present invention, a closure for a biological fluid collection device includes a cap having a first cap end, a second cap end, and defining a cap channel therein, the cap having a pierceable self-sealing stopper within a portion of the cap channel and a cap connection portion at the second cap end; a barrier in communication with a portion of the cap, the barrier protectively shielding a portion of the stopper; and an adapter having a first adapter end, a second adapter end, and defining an adapter channel therein, the adapter having an adapter connection portion at the first adapter end, the cap connection portion removably connectable with the adapter connection portion, wherein, with the cap connected to the adapter, the closure is connectable to a first blood collection device via the cap, and wherein, with the cap disconnected from the adapter, the closure is connectable to a second blood collection device via the first adapter end of the adapter.

In one configuration, the barrier comprises an undercut portion formed in the stopper. In another configuration, the barrier comprises a barrier wall portion formed with a portion of the cap. In yet another configuration, the barrier wall portion is transitionable between a first position and a second position. In one configuration, the barrier wall portion comprises a living hinge. In another configuration, the barrier protectively shields a portion of the first cap end. In yet another configuration, the barrier comprises a ring portion. In one configuration, the closure is connectable to a blood collection tube via the second adapter end of the adapter. In another configuration, with the closure connected to the blood collection tube, the closure seals the blood collection tube.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 2 is an elevation view of a closure in accordance with an embodiment of the present invention.

FIG. 3 is an exploded view of a closure in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
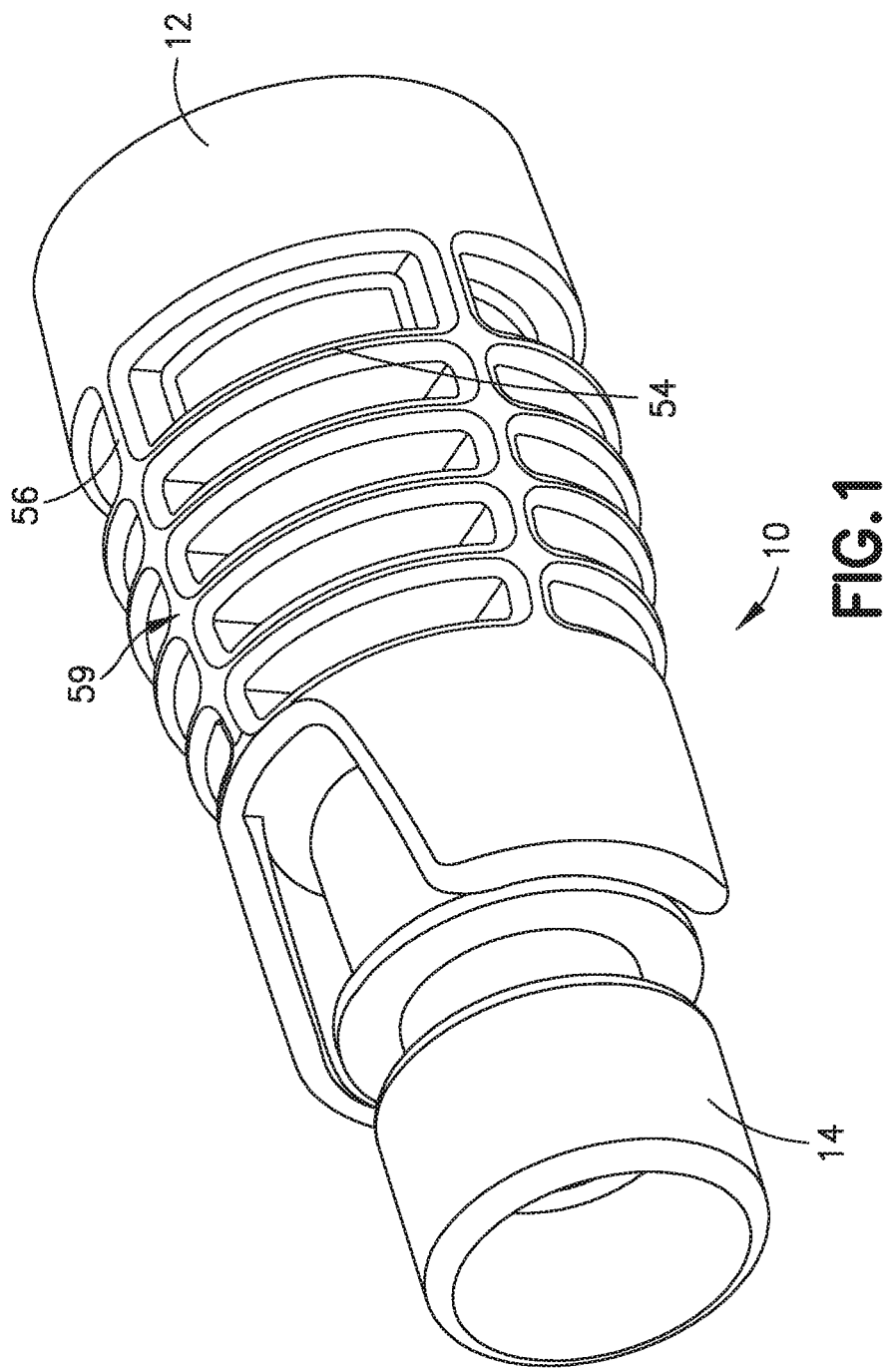
FIG. 1 is a perspective view of a closure in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides a closure for protectively sealing a biological fluid collection device or biological fluid collection tube. For example, in one embodiment, a closure of the present disclosure may protectively seal and secure to a vacuum containing blood collection tube such as a Vacutainer® blood collection tube commercially available from Becton, Dickinson and Company. In one embodiment, a closure of the present disclosure may protectively seal and secure to a micro-sample collection device. In other embodiments, a closure of the present disclosure may protectively seal and secure to other collection containers or blood collection devices.

Referring to FIGS. 1-8, a closure 10 includes a cap 12 and an adapter or connector 14. The closure 10 of the present disclosure allows for connection to multiple different blood collection devices. For example, in one embodiment, the closure 10 allows for connection to a first blood collection device 110 (FIGS. 6A-7) in a first configuration and connection to a second blood collection device 120 (FIG. 8) in a second configuration. An advantage of the closure 10 of the present disclosure is that it enables a single closure device to accommodate a variety of connection options.

Figure 6A:
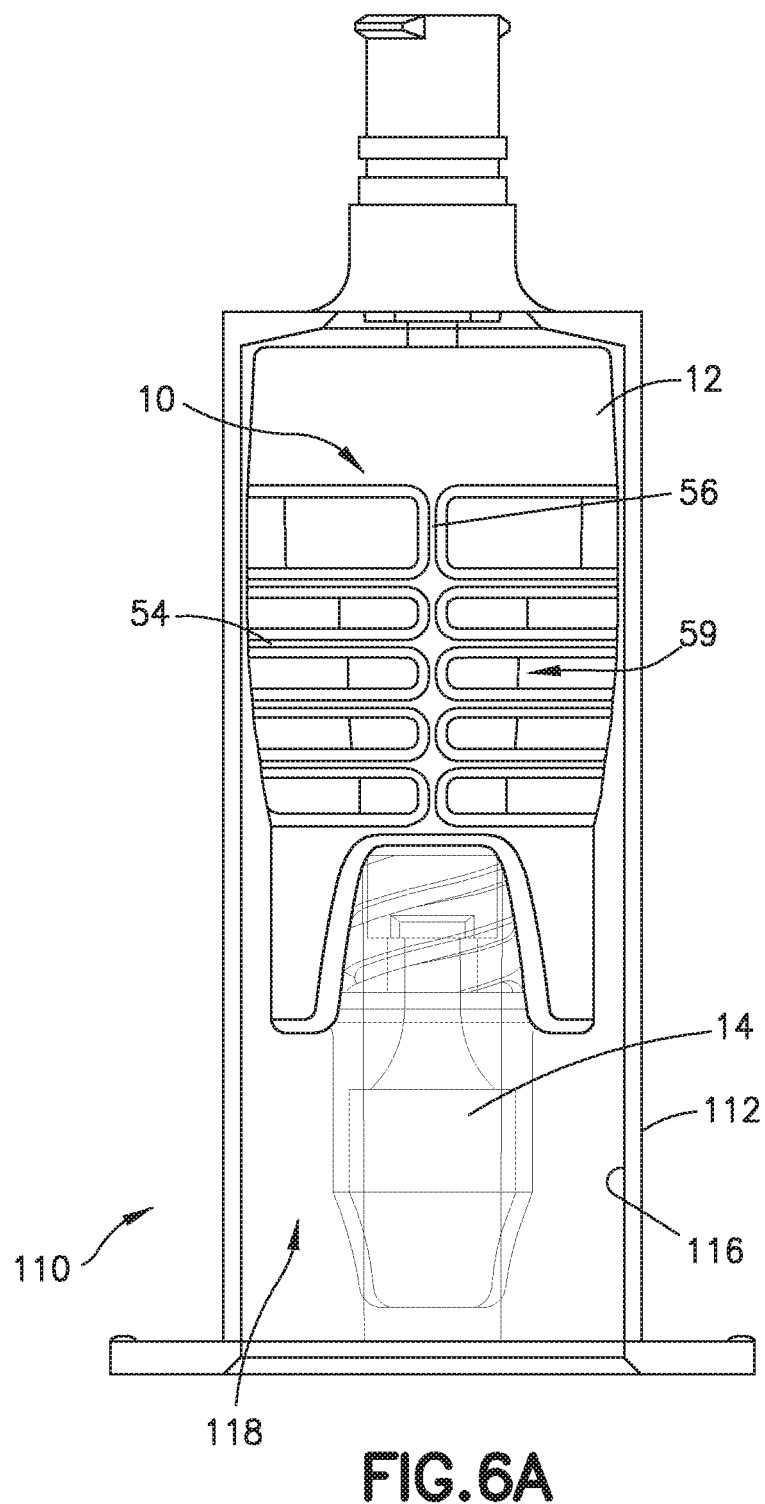
FIG. 6A is an elevation view of a closure connected to a first blood collection device in accordance with an embodiment of the present invention.

Referring to FIGS. 1-4, a closure 10 of the present disclosure includes a cap 12 and an adapter or connector 14. The closure 10 of the present disclosure allows for connection to multiple different blood collection devices. Referring to FIGS. 6A-7, in a first configuration, with the cap 12 connected to the adapter 14, the closure 10 may be connected to a first blood collection device 110. In one embodiment, the first blood collection device 110 includes a tube holder 112.

Figure 8:
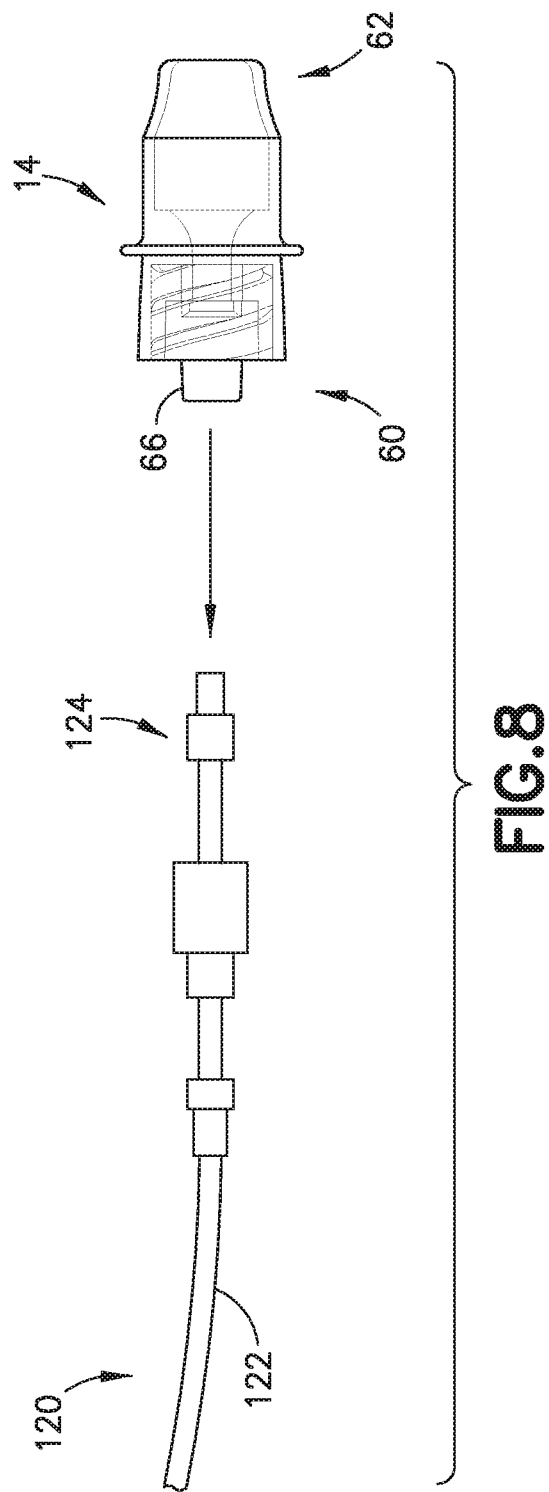
FIG. 8 is a perspective view of an adapter of a closure connected to a second blood collection device in accordance with an embodiment of the present invention.

Referring to FIG. 8, in a second configuration, with the cap 12 disconnected from the adapter 14, the closure 10 may be connected to a second blood collection device 120. In one embodiment, the second blood collection device 120 includes a line 122.

FIGS. 1-8 illustrate an exemplary embodiment of a closure of the present disclosure. Referring to FIGS. 1-4, the closure 10 includes a cap 12 and an adapter 14. In one embodiment, the cap 12 includes a first cap end 20, a second cap end 22, and defines a cap channel 24 therein. The cap 12 has a pierceable self-sealing stopper 26 within a portion of the cap channel 24 and a cap connection portion 28 at the second cap end 22. In one embodiment, the cap connection portion 28 comprises a first Luer connection portion.

Figure 4:
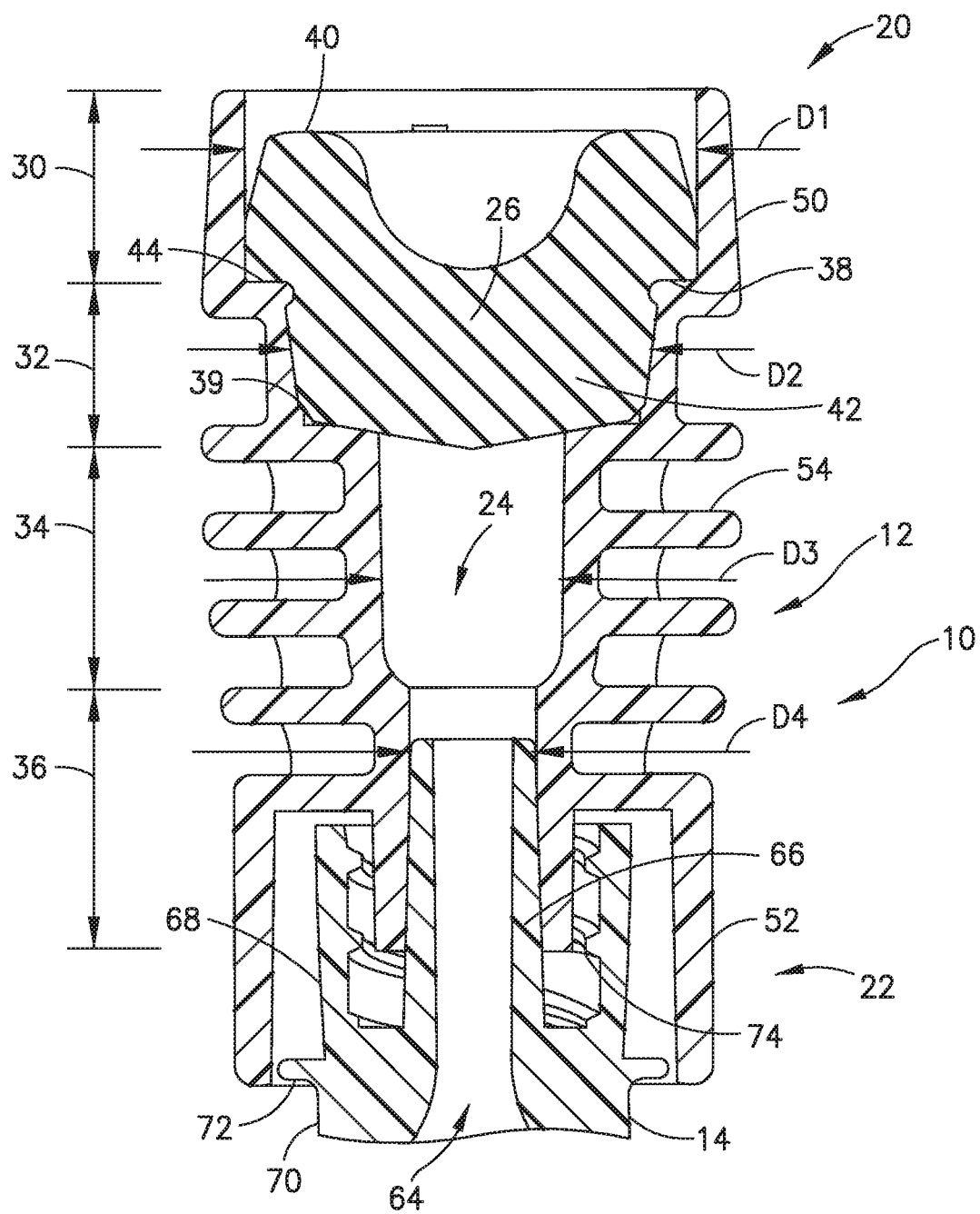
FIG. 4 is a cross-sectional view of a closure in accordance with an embodiment of the present invention.

Referring to FIG. 4, in one embodiment, the cap 12 defines a first cap channel portion 30 therein, a second cap channel portion 32 therein, a third cap channel portion 34 therein, and a fourth cap channel portion 36 therein. Referring to FIG. 4, the first cap channel portion 30 has a first diameter D1, the second cap channel portion 32 has a second diameter D2, the third cap channel portion 34 has a third diameter D3, and the fourth cap channel portion 36 has a fourth diameter D4. In one embodiment, the first diameter D1 is greater than the second diameter D2, the second diameter D2 is greater than the third diameter D3, and the third diameter D3 is greater than the fourth diameter D4. The first cap channel portion 30, the second cap channel portion 32, and the third cap channel portion 34 are configured to securely receive a stopper 26 within the cap 12. The fourth cap channel portion 36 is configured to securely receive a portion of the adapter 14.

In one embodiment, the cap 12 defines a first ledge portion 38 that is located between the first cap channel portion 30 and the second cap channel portion 32. Also, in one embodiment, the cap 12 defines a second ledge portion 39 that is located between the second cap channel portion 32 and the third cap channel portion 34.

Referring to FIG. 4, in one embodiment, the stopper 26 has a top portion 40, a bottom portion 42, and defines a shoulder portion 44 between the top portion 40 and the bottom portion 42.

The first cap channel portion 30, the second cap channel portion 32, and the third cap channel portion 34 are configured to securely receive a stopper 26 within the cap 12. For example, in one embodiment, the stopper 26 is contained within the cap channel 24 such that the top portion 40 of the stopper 26 is within the first cap channel portion 30 and the bottom portion 42 of the stopper 26 is within the second cap channel portion 32. In this manner, the stopper 26 is securely contained within the cap channel 24 such that the shoulder portion 44 of the stopper 26 contacts the first ledge portion 38 of the cap 12 and the bottom portion 42 of the stopper 26 contacts the second ledge portion 39 of the cap 12 to restrain the stopper 26 within the cap channel 24. Such engagement secures and restrains the stopper 26 within the cap channel 24 when the stopper 26 is punctured. For example, when a non-patient needle 114 (FIG. 6B) of a tube holder 112 contacts and pierces the stopper 26, the stopper 26 is prevented from significant relative movement relative to the cap 12.

In one embodiment, the cap 12 also includes a first wall shield portion 50, a second wall shield portion 52, radial ribs 54, and longitudinal ribs 56. Referring to FIG. 4, the second cap end 22 includes a second wall shield portion 52.

Referring to FIG. 4, the first cap end 20 includes a first wall shield portion 50 that protectively shields the stopper 26. For example, the first wall shield portion 50 provides a physical barrier that extends beyond the top portion 40 of the stopper 26 as shown in FIG. 4. In this manner, the stopper 26 is safely contained within the cap 12 and the first wall shield portion 50 provides protection from a portion of a blood sample on the stopper 26 splashing externally from the cap 12.

Referring to FIGS. 1-4, an outer surface 58 of the cap 12 includes radial ribs 54 and longitudinal ribs 56. The ribs 54, 56 provide gripping surfaces that make it easy for a user's fingers to grip the cap 12 of the closure 10. For example, the ribs 54, 56 provide ergonomically shaped surfaces that aid the user in manipulating the closure 10 and using the closure 10 in a blood collection procedure, and may provide multiple finger grip positions for the user.

Referring to FIGS. 6A-7, the ribs 54, 56 also provide touch point portions 59 that ensure that the closure 10 is properly aligned and positioned within a tube holder 112. For example, the touch point portions 59 extend outward so that the width of the cap 12 is slightly smaller than the inner diameter of the tube holder 112 and touch a portion of an interior surface 116 of the tube holder 112. This provides a centering and alignment mechanism when the closure 10 is inserted within a tube holder 112. In this manner, the cap 12 of the closure 10 is received within the tube holder 112 in a proper orientation, e.g., the cap 12 is properly centered within the tube holder 112 such that a non-patient needle 114 of the tube holder 112 is properly aligned with a stopper 26 of the closure 10.

In one embodiment, the adapter or connector 14 includes a first adapter end 60, a second adapter end 62, and defines an adapter channel 64 therein. The adapter 14 has an adapter connection portion 66 at the first adapter end 60. Referring to FIG. 3, in one embodiment, the adapter 14 includes a first portion 68, a second portion 70, and a flange portion 72 between the first portion 68 and the second portion 70. In one embodiment, the adapter connection portion 66 comprises a second Luer connection portion for mating connection with the first Luer connection portion of the cap connection portion 28.

Referring to FIGS. 1-4, the adapter 14 is removably connectable to the cap 12. For example, the adapter connection portion 66 is removably connectable with the cap connection portion 28 of the cap 12. In one embodiment, the cap connection portion 28 comprises a first Luer connection portion and the adapter connection portion 66 comprises a second Luer connection portion for mating connection with the first Luer connection portion. In one embodiment, the connection portions 28, 66 form an ISO standard Luer interface. In one embodiment, the connection portions 28, 66 form a spin lock Luer interface. For example, the adapter connection portion 66 may include a Luer lock thread portion 74. In another embodiment, the connection portions 28, 66 form a slip lock Luer interface. The cap connection portion 28 and the adapter connection portion 66 may be threaded or snap-fit together to form a secure connection.

With the adapter 14 connected to the cap 12, the adapter 14 is locked to the cap 12, i.e., the adapter 14 and the cap 12 are protectively sealed theretogether. Referring to FIG. 4, with the adapter 14 connected to the cap 12, the cap channel 24 is in fluid communication with the adapter channel 64.

Referring to FIG. 4, with the cap 12 connected to the adapter 14, the second wall shield portion 52 of the cap 12 protectively shields the first adapter end 60 and the first portion 68 of the adapter 14. For example, the second wall shield portion 52 provides a physical barrier that extends beyond the flange portion 72 of the adapter 14 as shown in FIG. 4. In this manner, the second wall shield portion 52 and the flange portion 72 form a protective physical barrier that protectively shields the first adapter end 60 and the first portion 68 of the adapter 14.

Figure 5:
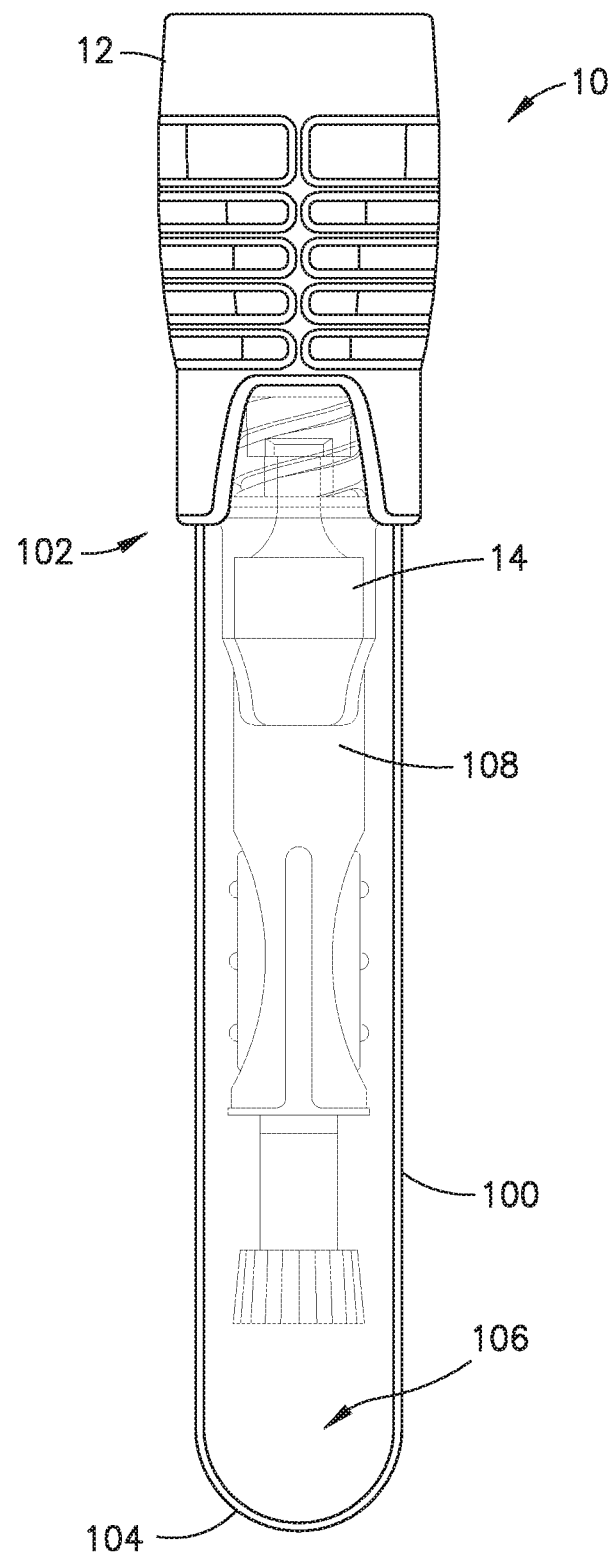
FIG. 5 is a perspective view of a closure connected to a blood collection tube in accordance with an embodiment of the present invention.

Referring to FIG. 5, a closure 10 of the present disclosure is able to protectively seal a blood collection tube, outer housing of a micro-containment device, or other collection device 100. As described above, in one embodiment, a closure of the present disclosure may protectively seal and secure to a vacuum containing blood collection tube such as a Vacutainer® blood collection tube commercially available from Becton, Dickinson and Company. In one embodiment, a closure of the present disclosure may protectively seal and secure to a micro-sample collection device or micro-containment device. In other embodiments, a closure of the present disclosure may protectively seal and secure to other collection containers or blood collection devices.

Referring to FIG. 5, in one exemplary embodiment, the closure 10 is connectable to a blood collection tube 100 via the second adapter end 62 of the adapter 14. With the closure 10 connected to the blood collection tube 100, the closure 10 seals the blood collection tube 100. Referring to FIG. 5, the blood collection tube 100 includes a first end 102, a closed second end 104, and defines a cavity 106 therein. Referring to FIG. 5, in one embodiment, the closure 10 and the blood collection device or micro-containment device 100 is compatible with a collection module 108. The collection module 108 provides a biological fluid collection device that receives a sample and provides flow-through blood stabilization technology and a precise sample dispensing function for point-of-care and near patient testing applications. In this manner, the closure 10, the blood collection device or micro-containment device 100, and the collection module 108 is able to effectuate distributed mixing of a sample stabilizer within a blood sample and dispense the stabilized sample in a controlled manner. In this manner, the closure 10, the blood collection device or micro-containment device 100, and the collection module 108 enables blood micro-sample management, e.g., passive mixing with a sample stabilizer and controlled dispensing, for point-of-care and near patient testing applications Referring to FIG. 5, the closure 10 can be engaged with and protectively seal the first end 102 of the blood collection tube 100 to seal the cavity 106. The closure 10 allows for the safe introduction of a blood sample into the cavity 106 of the blood collection tube 100 as described in more detail below.

As described above, the closure 10 of the present disclosure allows for connection to multiple different blood collection devices. For example, in one embodiment, the closure 10 allows for connection to a first blood collection device 110 (FIGS. 6A-7) in a first configuration and connection to a second blood collection device 120 (FIG. 8) in a second configuration. An advantage of the closure 10 of the present disclosure is that it enables a single closure device to accommodate a variety of connection options.

Figure 6B:
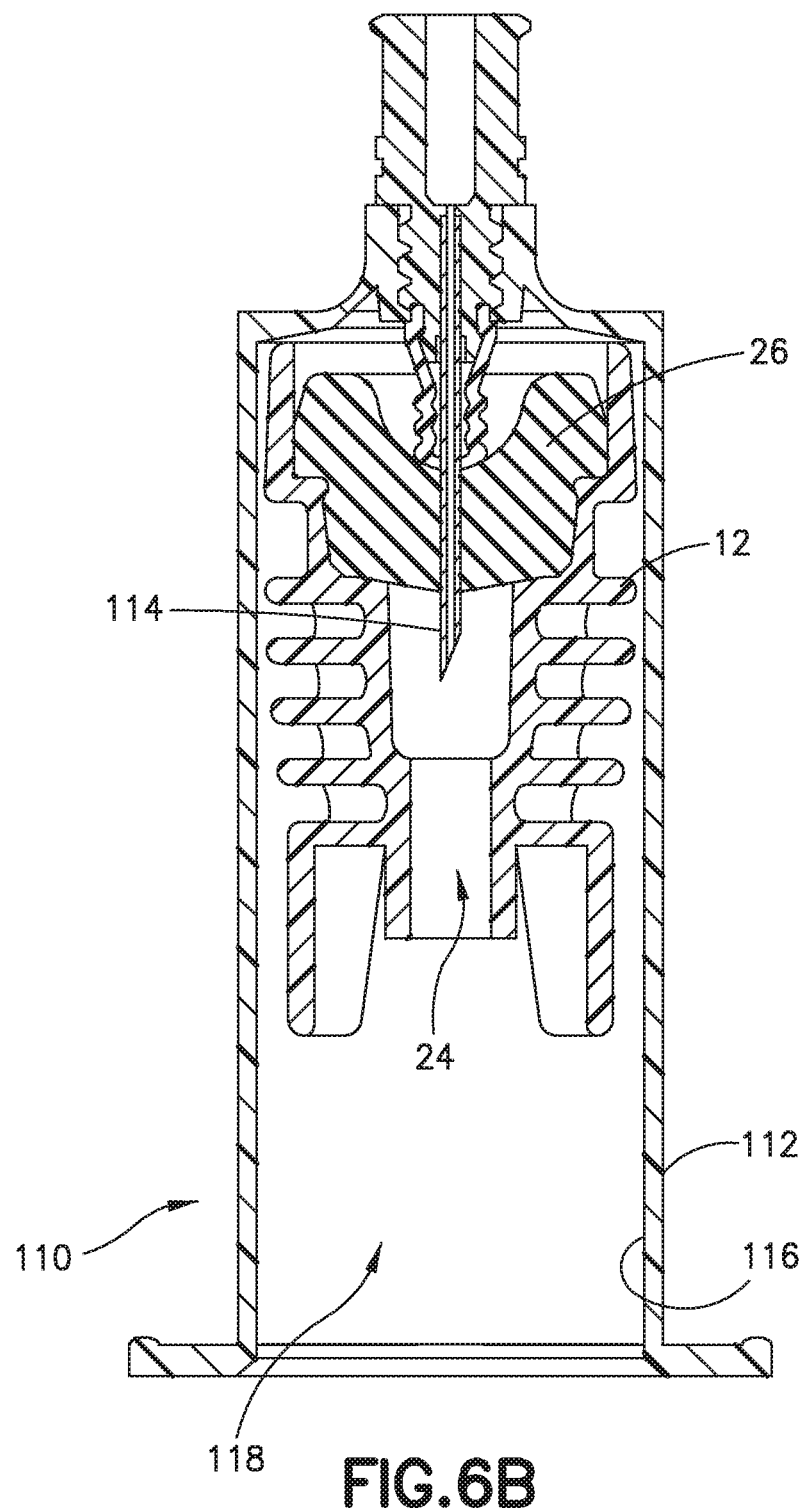
FIG. 6B is a cross-sectional view of a portion of a closure connected to a first blood collection device in accordance with an embodiment of the present invention.
Figure 7:
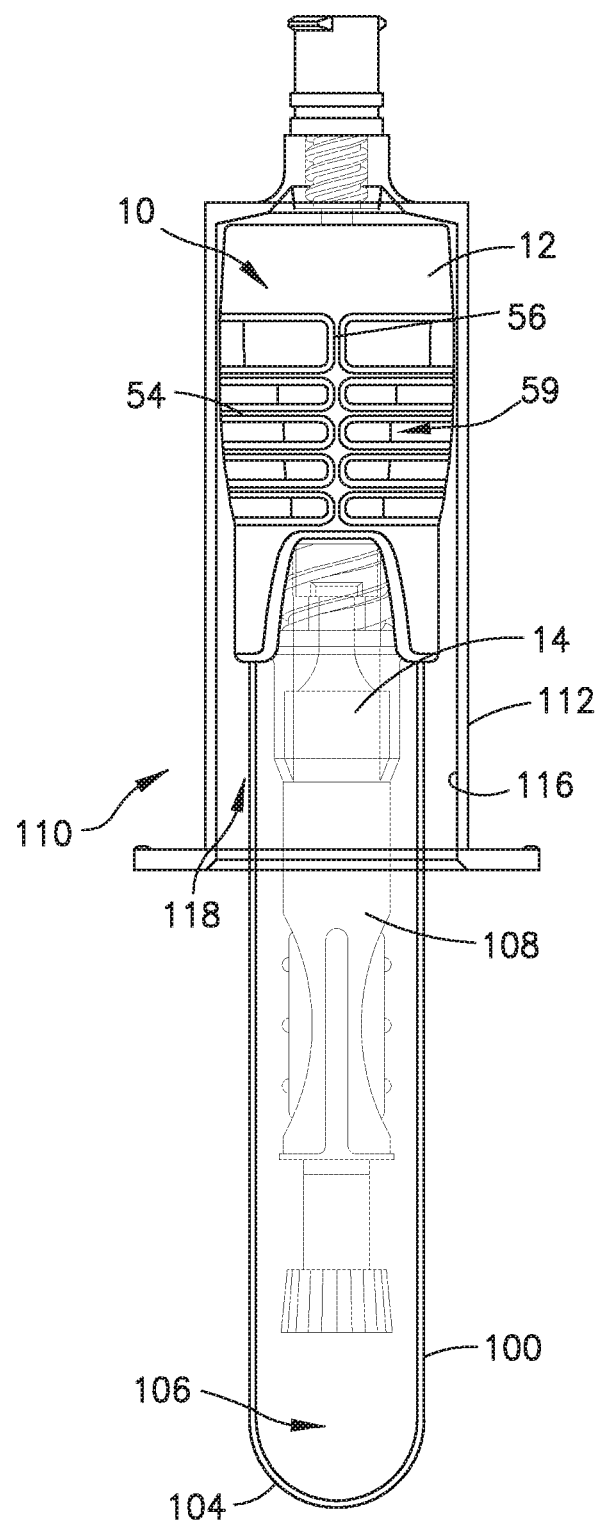
FIG. 7 is a perspective view of a closure with a blood collection tube and connected to a first blood collection device in accordance with an embodiment of the present invention.

Referring to FIGS. 6A-7, in a first configuration, with the cap 12 connected to the adapter 14, the closure 10 may be connected to a first blood collection device 110 via the cap 12. In one embodiment, the first blood collection device 110 includes a tube holder 112 having a non-patient needle 114 (FIG. 6B) through which biological fluid is passed, and an interior wall or surface 116 which defines a tube cavity 118.

Referring to FIGS. 6A-7, a closure 10 may be properly positioned within the tube cavity 118 of a tube holder 112. For example, the touch point portions 59 of the cap 12 provide a centering and alignment mechanism when the closure 10 is inserted within the tube holder 112. In this manner, the cap 12 of the closure 10 is received within the tube holder 112 in a proper orientation, e.g., the cap 12 is properly centered within the tube holder 112 such that a non-patient needle 114 of the tube holder 112 is properly aligned with a stopper 26 of the closure 10.

With the closure 10 properly positioned within the tube cavity 118 of the tube holder 112, a user exerts a force on the blood collection tube 100 to move the closure 10 into engagement with the non-patient needle 114 (FIG. 6B) of the tube holder 112. For example, the non-patient needle 114 contacts and pierces the stopper 26 such that the non-patient needle 114 is inserted into a portion of the cap channel 24. In this manner, the non-patient needle 114 is in fluid communication with the cavity 106 of the blood collection tube 100 via the cap channel 24 and the adapter channel 64 (FIG. 4).

Referring to FIGS. 4 and 6A-7, as the non-patient needle 114 contacts and pierces the stopper 26, the stopper 26 is restrained within the cap channel 24, e.g., the stopper 26 is prevented from significant relative movement relative to the cap channel 24 of the cap 12. For example, the shoulder portion 44 of the stopper 26 contacting the first ledge portion 38 of the cap 12 and the bottom portion 42 of the stopper 26 contacting the second ledge portion 39 of the cap 12 provide physical barriers that prevent significant relative movement of the stopper 26 relative to the cap 12 as the non-patient needle 114 contacts and pierces the stopper 26.

Next, a biological fluid sample, e.g., a blood sample, is pulled into the cavity 106 of the blood collection tube 100 from the tube holder 112 by the draw of a vacuum. Such a blood sample travels through the non-patient needle 114 of the tube holder 112, the cap channel 24 of the cap 12, the adapter channel 64 of the adapter 14, to the cavity 106 of the blood collection tube 100. Once blood sample collection is complete, the blood collection tube 100, including the closure 10, may be removed from the tube holder 112. After the closure 10 and the blood collection tube 100 are removed from the tube holder 112, the closure protectively seals the blood sample within the blood collection tube 100.

With conventional devices, during removal of a collection tube from a tube holder, droplets of blood can splash and accumulate on exit points of the collection tube. Advantageously, a closure of the present disclosure is able to protectively shield the stopper 26 and the cap 12 and provide protection from a blood sample contacting a healthcare practitioner. For example, as discussed above, referring to FIG. 4, the first cap end 20 includes a first wall shield portion 50 that protectively shields the stopper 26. For example, the first wall shield portion 50 provides a physical barrier that extends beyond the top portion 40 of the stopper 26 as shown in FIG. 4. In this manner, the stopper 26 is safely contained within the cap 12 and the first wall shield portion 50 provides protection from a portion of a blood sample on the stopper 26 splashing externally from the cap 12.

Furthermore, a closure 10 of the present disclosure provides additional guards for protectively shielding the stopper 26 and the cap 12 and providing protection from a blood sample contacting a healthcare practitioner. For example, in one embodiment, the closure 10 includes a barrier that protectively shields a portion of the stopper 26 and/or protectively shields a portion of the first cap end 20. In one embodiment, the barrier is in communication with a portion of the cap 12, and the barrier protectively shields a portion of the stopper 26.

Figure 9:
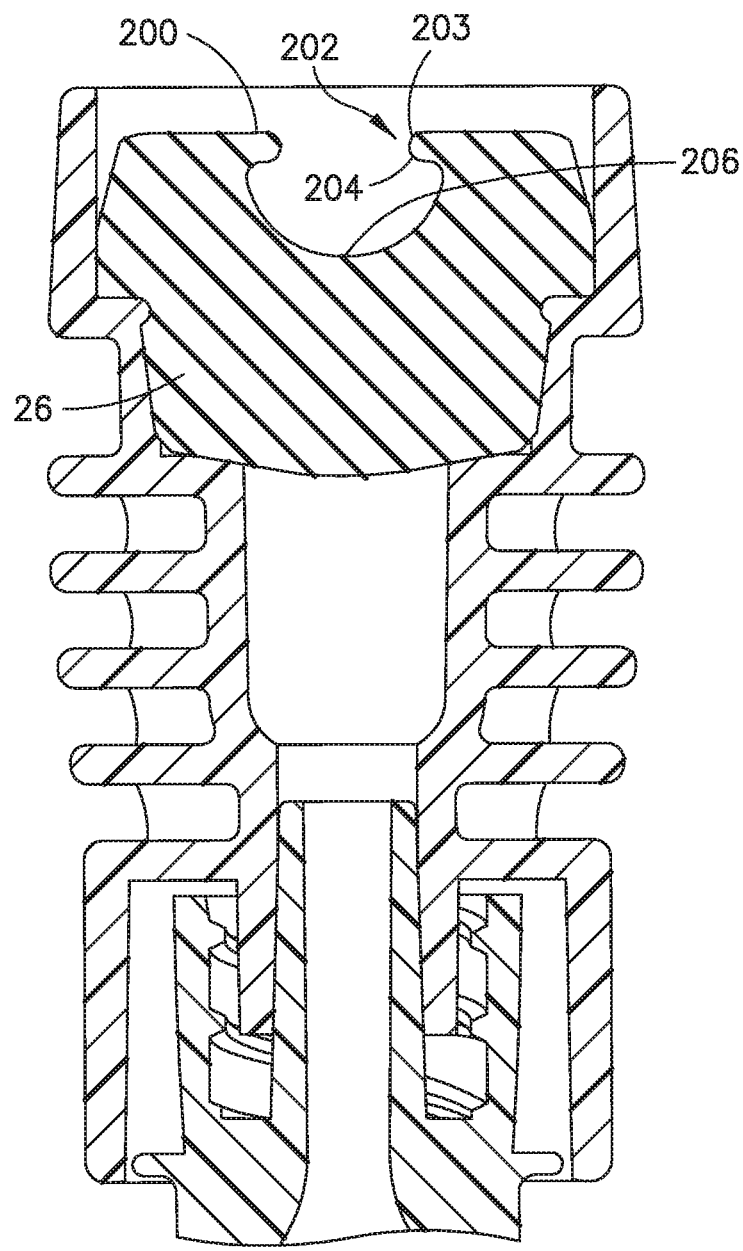
FIG. 9 is a cross-sectional view of a stopper having a barrier in accordance with an embodiment of the present invention.

Referring to FIG. 9, in one embodiment, a barrier 200 of the present disclosure comprises an undercut portion 202 that is formed in the stopper 26. The undercut portion 202 includes an inferior surface 204. The undercut portion 202 includes inwardly extending protective shield portions 203. Underneath the protective shield portions 203 is formed a bowl portion 206.

During completion of a blood sample collection procedure and while removing the closure 10 from a tube holder 112, any blood that splashes contacts the inferior surface 204 underneath the inwardly extending protective shield portions 203 of the undercut portion 202. The undercut portion 202 and the inwardly extending protective shield portions 203 are sized to be large enough to hold blood droplets in place with surface tension. In this manner, the inwardly extending protective shield portions 203 provide additional protection from droplets of blood from splashing externally from the cap 12 thereby reducing the risk of blood from contacting a healthcare practitioner. The barrier 200 ensures that any droplets of blood that splash are safely shielded on the inferior surface 204 underneath the inwardly extending protective shield portions 203 of the undercut portion 202.

Figure 10:
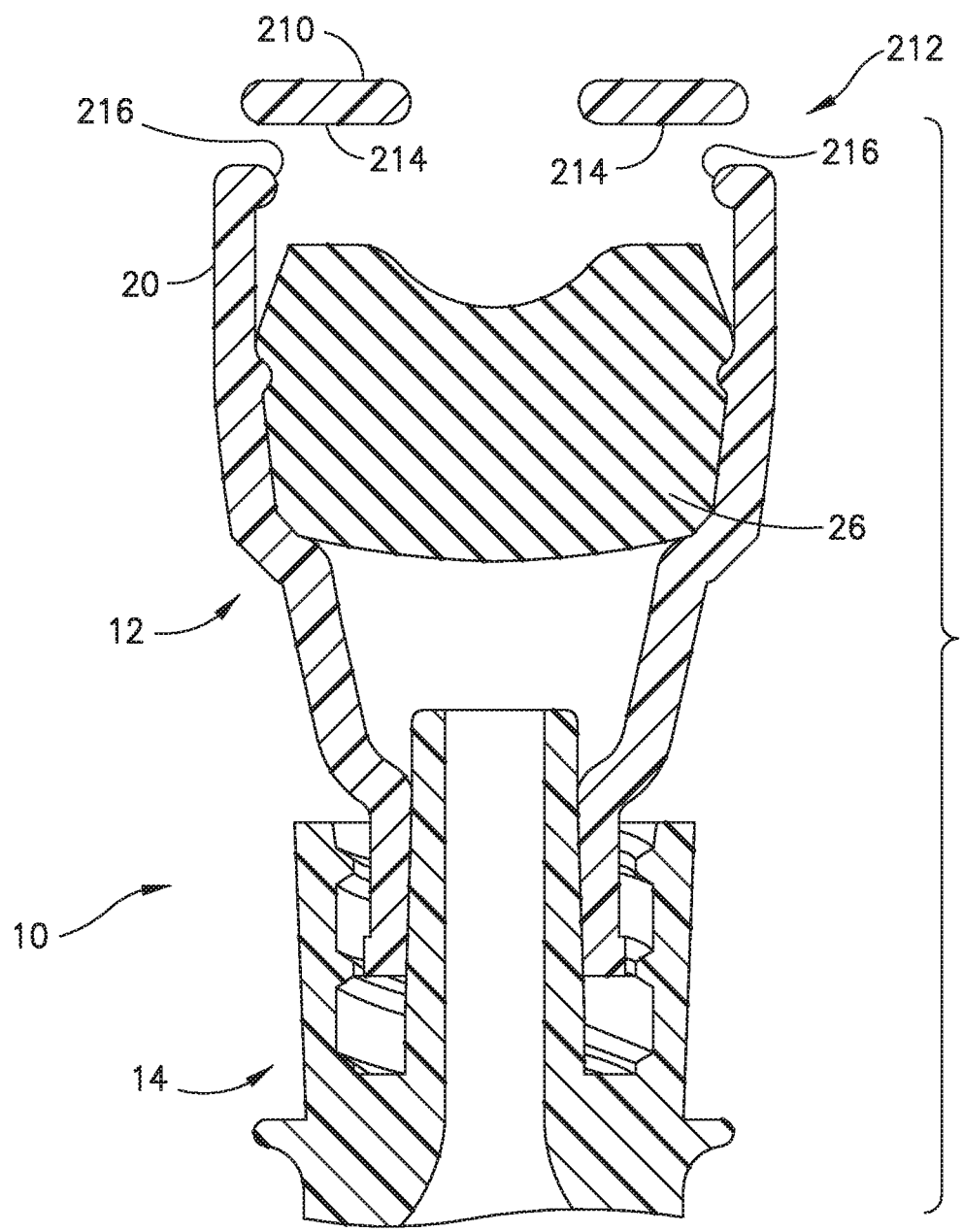
FIG. 10 is an exploded cross-sectional view of a closure having a barrier in accordance with another embodiment of the present invention.

Referring to FIG. 10, in one embodiment, a barrier 210 of the present disclosure comprises a ring portion or barrier wall portion 212. The ring portion 212 includes an inferior surface 214. The ring portion 212 is in communication with a portion of the cap 12. For example, in one embodiment, the ring portion 212 can be a cap portion that is removably connectable with the first cap end 20 of the cap 12.

In one embodiment, the barrier wall portion 212 is transitionable between a first or open position, in which the barrier wall portion 212 does not cover the stopper 26, and a second or closed position, in which the barrier wall portion 212 covers and protectively shields the stopper 26. In one embodiment, the barrier wall portion 212 of the barrier 210 may securely snap into place and connect to a connection portion 216 such that the barrier wall portion 212 of the barrier 210 is movable between the first or open position and the second or closed position. In one embodiment, the barrier wall portion 212 comprises a living hinge with a portion of the cap 12.

Figure 11:
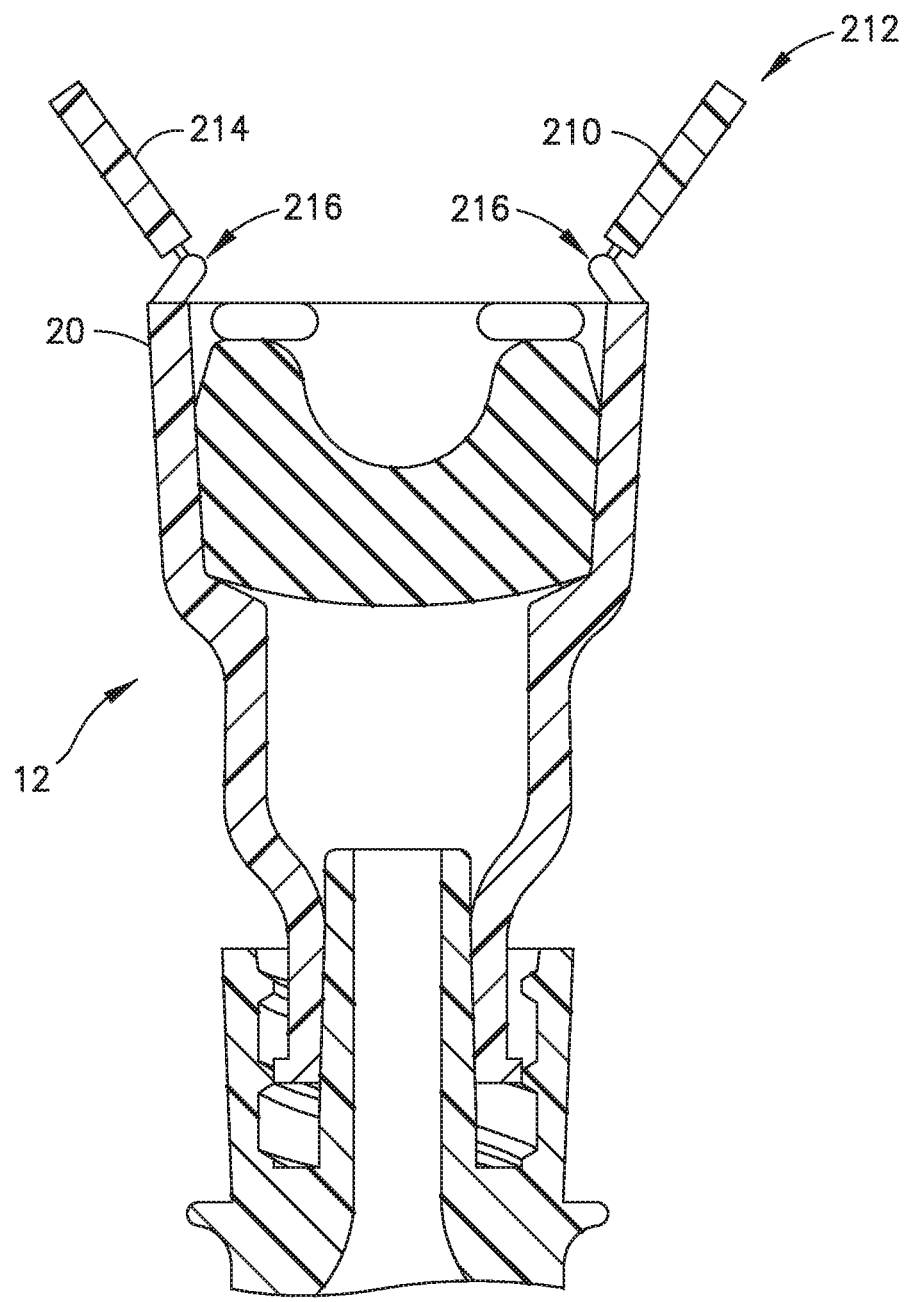
FIG. 11 is a cross-sectional view of a barrier connected to a closure in an open position in accordance with another embodiment of the present invention.

Referring to FIG. 10, in one embodiment, the first cap end 20 of the cap 12 may include a connection portion 216. FIG. 10 illustrates an exploded view of the barrier 210 above the connection portion 216. In one embodiment, the barrier 210 may securely snap into place and connect to the connection portion 216 such that the barrier 210 is movably between a closed position and an open position. In one embodiment, referring to FIG. 11, the ring portion 212 may include two separate portions that are each movably connected to the connection portion 216. In this manner, as shown in FIG. 11, each ring portion 212 may pivot about a respective connection portion 216 between an open and closed position.

Figure 18:
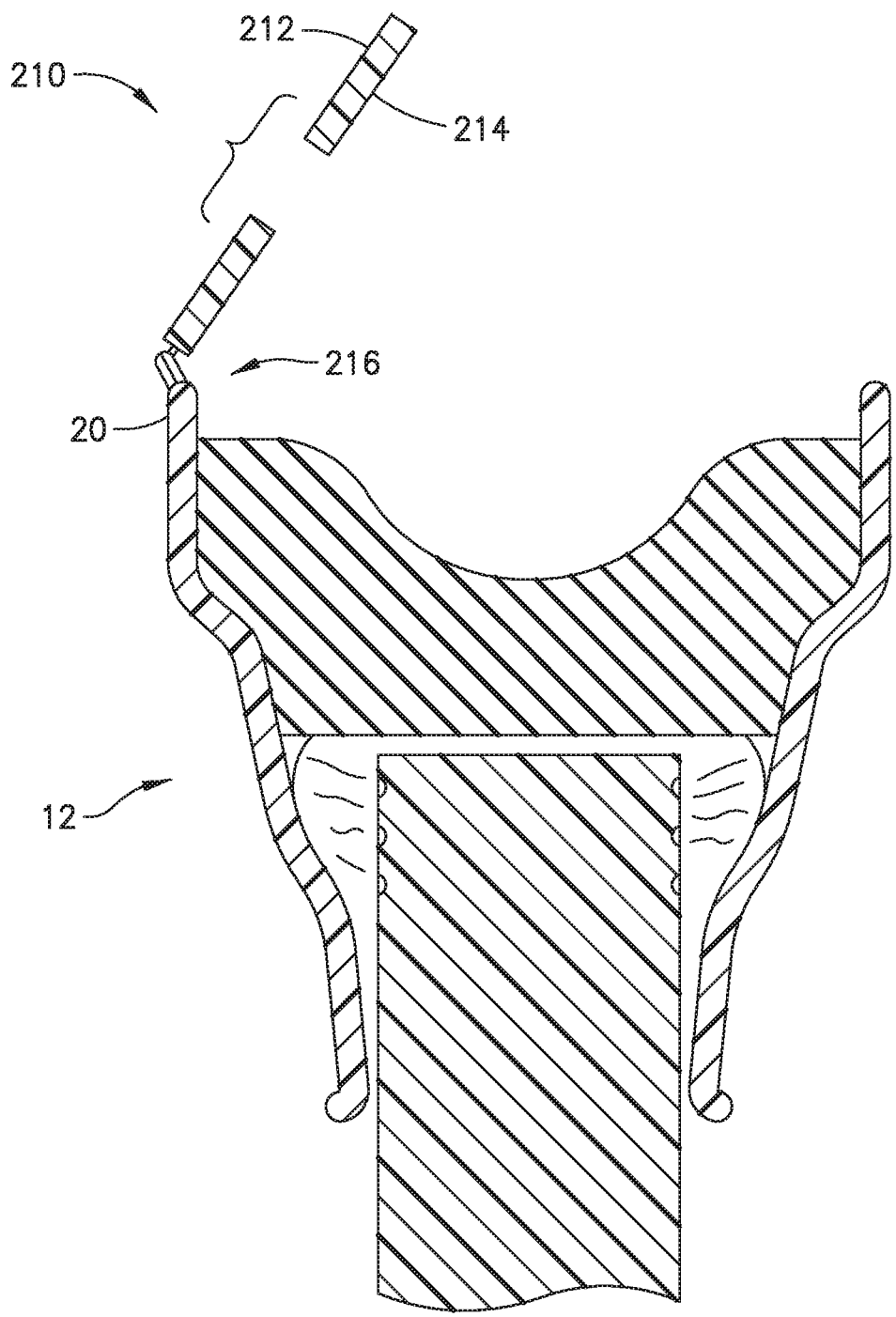
FIG. 18 is a cross-sectional view of a closure having a barrier in accordance with another embodiment of the present invention.

In another embodiment, referring to FIG. 18, the ring portion 212 may include one piece with an aperture in the middle and only be secured to one connection portion 216. In this manner, as shown in FIG. 18, the barrier 210 may swing open like a door between an open position and a closed position.

During completion of a blood sample collection procedure and while removing the closure 10 from a tube holder 112, and with the barrier wall portion 212 in the closed position, any blood that splashes contacts the inferior surface 214 of the barrier wall portion 212 of the barrier 210. The barrier wall portion 212 is sized to be large enough to hold blood droplets in place with surface tension. In this manner, the barrier wall portion 212 provides additional protection from droplets of blood from splashing externally from the cap 12 thereby reducing the risk of blood from contacting a healthcare practitioner. The barrier wall portion 212 ensures that any droplets of blood that splash are safely shielded on the inferior surface 214 of the barrier wall portion 212.

Referring to FIG. 8, in a second configuration, with the cap 12 disconnected from the adapter 14, the closure 10 may be connected to a second blood collection device 120 via the first adapter end 60 of the adapter 14. As discussed above, the cap 12 is removably connectable to the adapter 14. The cap 12 may be easily disconnected from the adapter 14 by disconnecting the cap connection portion 28 and the adapter connection portion 66. In one embodiment, the second blood collection device 120 includes a line 122 and a standard Luer interface 124.

Referring to FIG. 8, the adapter 14 is removably connectable to the line 122. For example, in one embodiment, the adapter connection portion 66 is removably connectable with the standard Luer interface 124 of the line 122. In one embodiment, the adapter connection portion 66 comprises a Luer connection portion for mating connection with the standard Luer interface 124 of the line 122.

Referring to FIGS. 12-15, in one embodiment, the cap 12 and the adapter 14 may be formed of a single integral component. In such an embodiment, the cap 12 and the adapter 14 may be formed of the same material in a single manufacturing process.

Figure 12:
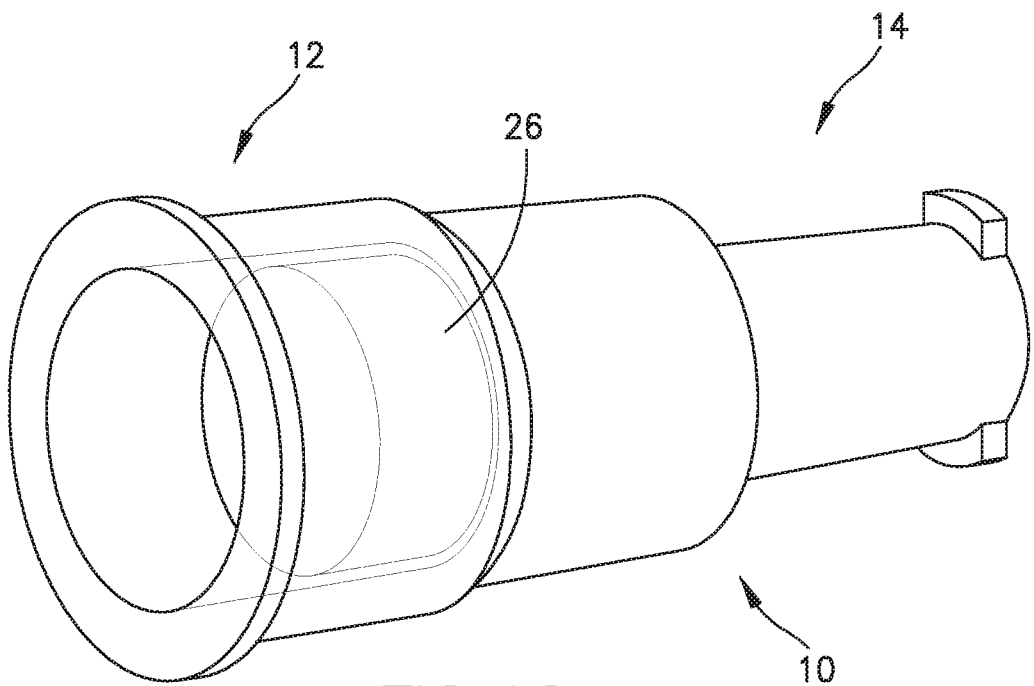
FIG. 12 is a perspective view of a closure in accordance with another embodiment of the present invention.
Figure 13:
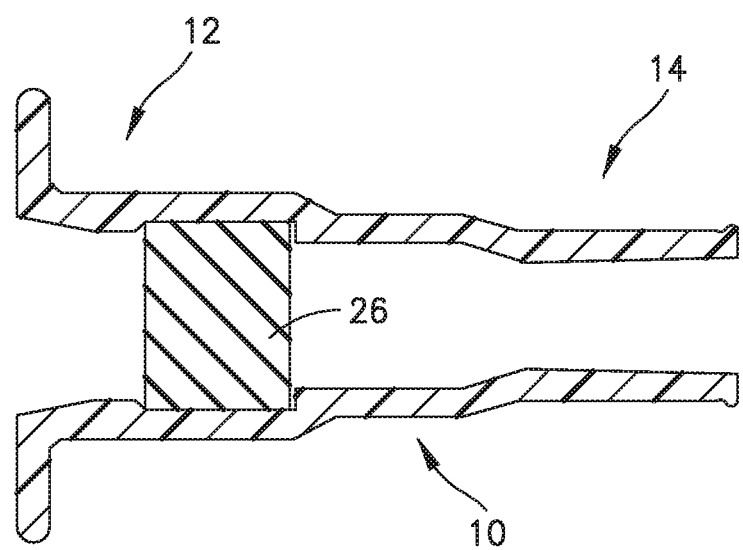
FIG. 13 is a cross-sectional view of the closure of FIG. 12 in accordance with an embodiment of the present invention.

Referring to FIGS. 12 and 13, in one embodiment, the stopper 26 is cylindrical. In such an embodiment, the cylindrical stopper 26 can be snap-fit into secure engagement with the closure 10 as shown in FIG. 13.

Figure 14:
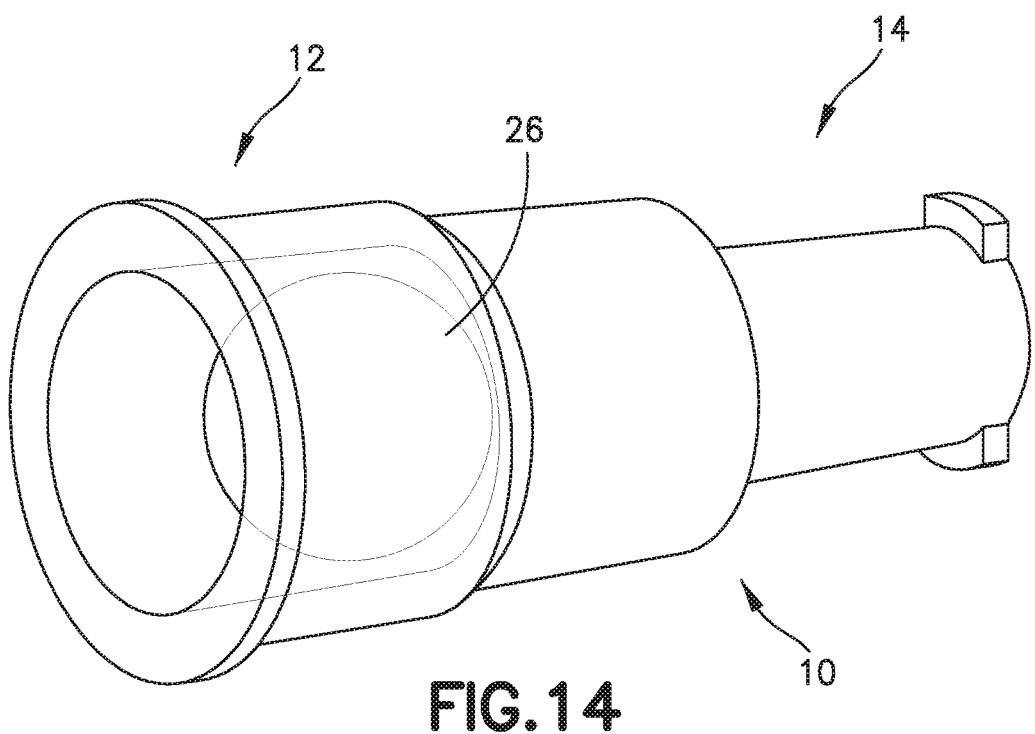
FIG. 14 is a perspective view of a closure in accordance with another embodiment of the present invention.
Figure 15:
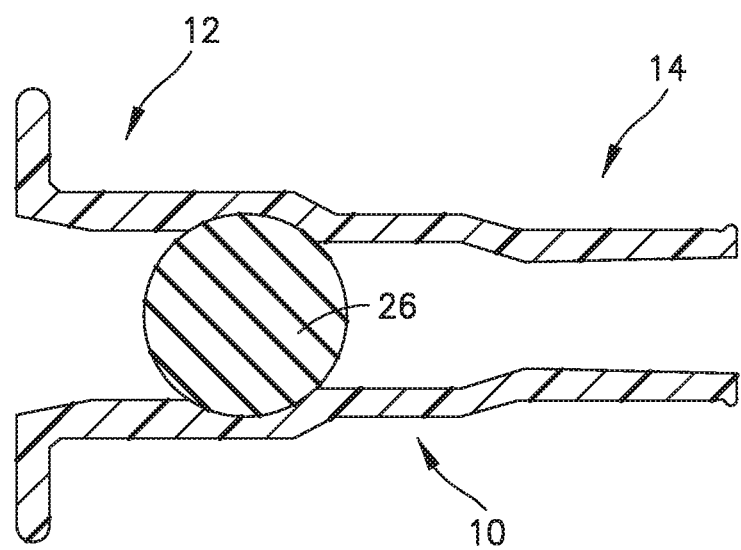
FIG. 15 is a cross-sectional view of the closure of FIG. 14 in accordance with an embodiment of the present invention.

Referring to FIGS. 14 and 15, in one embodiment, the stopper 26 is spherical. In such an embodiment, the spherical stopper 26 can be snap-fit into secure engagement with the closure 10 as shown in FIG. 15. The spherical shape of the stopper 26 can make it easier to snap-fit the stopper 26 into engagement with the closure 10.

Figure 16:
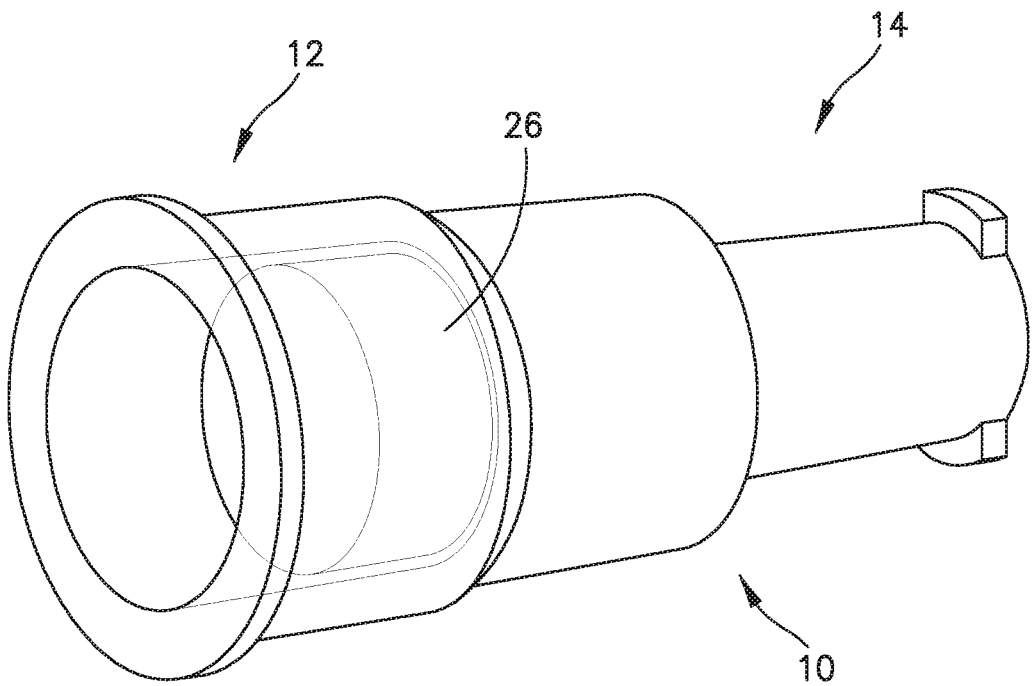
FIG. 16 is a perspective view of a closure in accordance with another embodiment of the present invention.
Figure 17:
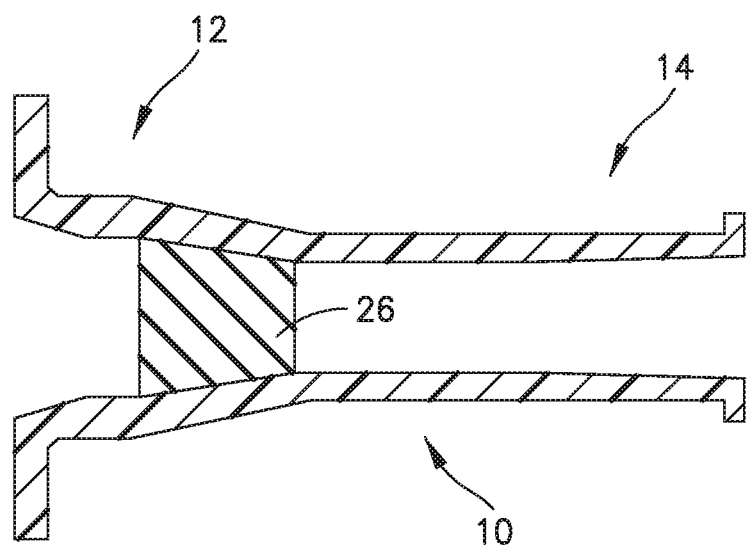
FIG. 17 is a cross-sectional view of the closure of FIG. 16 in accordance with an embodiment of the present invention.

Referring to FIGS. 16 and 17, in one embodiment, the cap 12 and the adapter 14 may be formed of a single integral component. In one embodiment, the cap 12, the adapter 14, and the stopper 26 may be formed in a two-shot molding process. For example, the cap 12 and the adapter 14 may be formed of a hard plastic and the stopper 26 may be formed of a thermoplastic elastomer.

Figure 19:
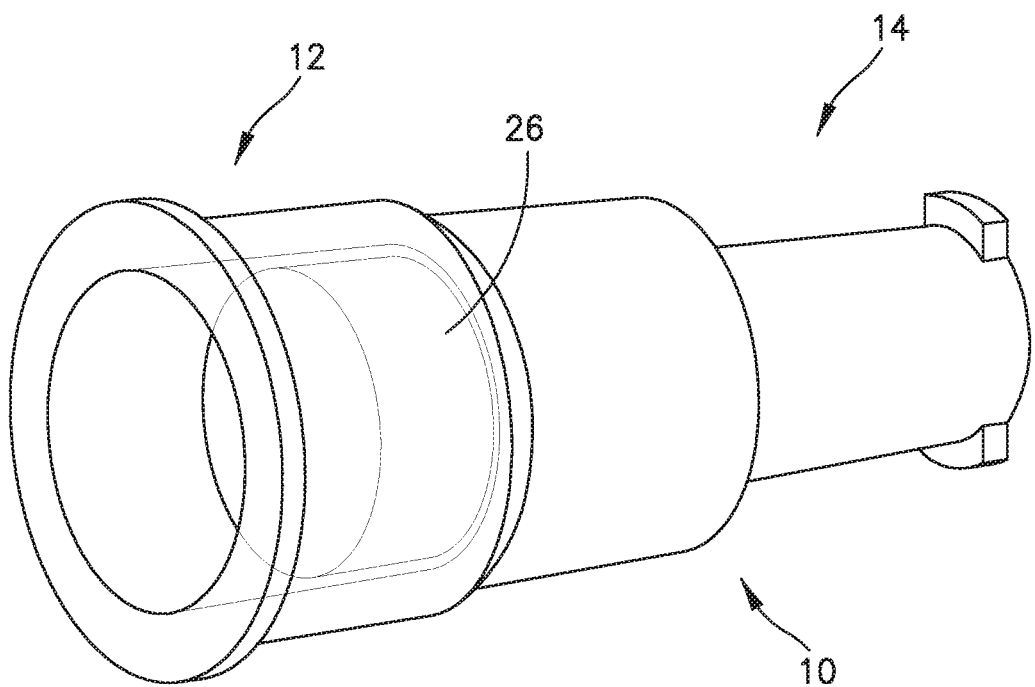
FIG. 19 is a perspective view of a closure in accordance with another embodiment of the present invention.
Figure 20:
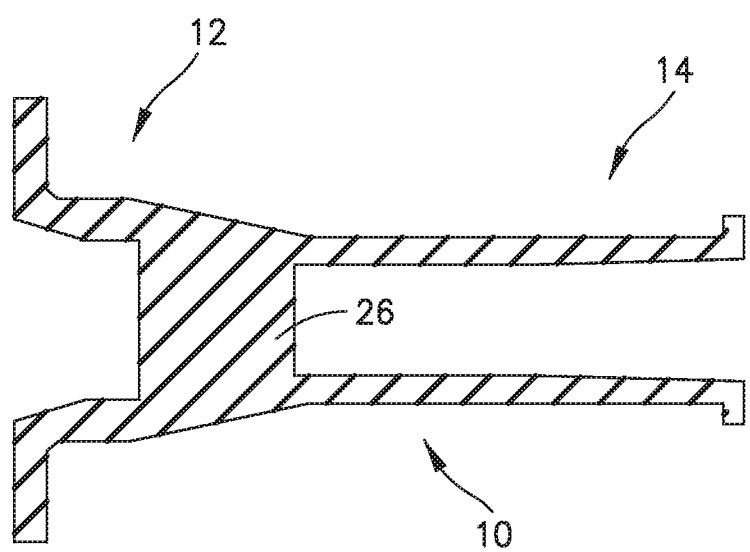
FIG. 20 is a cross-sectional view of the closure of FIG. 19 in accordance with an embodiment of the present invention.

Referring to FIGS. 19 and 20, in one embodiment, the cap 12, the adapter 14, and the stopper 26 may all be formed of a single integral component. In one embodiment, the cap 12, the adapter 14, and the stopper 26 may be formed in a one-shot molding process. For example, the cap 12, the adapter 14, and the stopper 26 may all be formed of a thermoplastic elastomer.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A closure for a biological fluid collection device, comprising:
   a cap having a first cap end, a second cap end, and defining a cap channel therein, the cap having a pierceable self-sealing stopper within a portion of the cap channel and a cap connection portion at the second cap end; and an adapter having a first adapter end, a second adapter end, and defining an adapter channel therein, the adapter having an adapter connection portion at the first adapter end, the cap connection portion removably connectable with the adapter connection portion, wherein, with the cap connected to the adapter, the closure is connectable to a first blood collection device via the cap, wherein, with the cap disconnected from the adapter, the closure is connectable to a second blood collection device via the first adapter end of the adapter; and wherein the closure is removably connectable to a blood collection tube via the second adapter end of the adapter, with the second adapter end of the adapter sealing the blood collection tube when connected thereto.

2. The closure of claim 1, wherein the cap defines a first cap channel portion therein having a first diameter, and a second cap channel portion therein having a second diameter, wherein the first diameter is greater than the second diameter.

3. The closure of claim 2, wherein the stopper has a top portion and a bottom portion, the stopper contained within the cap channel such that the top portion of the stopper is within the first cap channel portion and the bottom portion of the stopper is within the second cap channel portion.

4. The closure of claim 3, wherein the stopper defines a shoulder portion between the top portion and the bottom portion and the cap defines a ledge portion between the first cap channel portion and the second cap channel portion, wherein the stopper is contained within the cap channel such that the shoulder portion of the stopper contacts the ledge portion of the cap.

5. The closure of claim 1, wherein the first blood collection device is a tube holder.

6. The closure of claim 1, wherein the second blood collection device is a line.

7. The closure of claim 1, wherein the cap connection portion comprises a first Luer connection portion and the adapter connection portion comprises a second Luer connection portion for mating connection with the first Luer connection portion.

8. The closure of claim 1, wherein the first cap end includes a first wall shield portion that protectively shields the stopper, and the second cap end includes a second wall shield portion that protectively shields the first adapter end.

9. The closure of claim 1, wherein, with the cap connected to the adapter, the cap channel is in fluid communication with the adapter channel.

10. The closure of claim 1, wherein the second adapter end of the adapter is configured to be inserted into an open end of the blood collection tube, to seal a cavity within the blood collection tube.

11. A closure for a biological fluid collection device, comprising:

a cap having a first cap end, a second cap end, and defining a cap channel therein, the cap having a pierceable self-sealing stopper within a portion of the cap channel and a cap connection portion at the second cap end;

a barrier in communication with a portion of the cap, the barrier protectively shielding a portion of the stopper; and an adapter having a first adapter end, a second adapter end, and defining an adapter channel therein, the adapter having an adapter connection portion at the first adapter end, the cap connection portion removably connectable with the adapter connection portion, wherein, with the cap connected to the adapter, the closure is connectable to a first blood collection device via the cap, wherein, with the cap disconnected from the adapter, the closure is connectable to a second blood collection device via the first adapter end of the adapter, and wherein the closure is removably connectable to a blood collection tube via the second adapter end of the adapter, with the second adapter end of the adapter sealing the blood collection tube when connected thereto.

12. The closure of claim 11, wherein the barrier comprises an undercut portion formed in the stopper.

13. The closure of claim 11, wherein the barrier comprises a barrier wall portion formed with a portion of the cap.

14. The closure of claim 13, wherein the barrier wall portion is transitionable between a first position and a second position.

15. The closure of claim 13, wherein the barrier wall portion comprises a living hinge.

16. The closure of claim 13, wherein the barrier protectively shields a portion of the first cap end.

17. The closure of claim 11, wherein the barrier comprises a ring portion.

18. The closure of claim 11, wherein the second adapter end of the adapter is configured to be inserted into an open end of the blood collection tube, to seal a cavity within the blood collection tube.

* * * * *

UNITED STATES PATENT AND TRADEMARK OFFICE
CERTIFICATE OF CORRECTION

| | | |
|---|---|---|
| PATENT NO. | : 12,127,836 B2 | Page 1 of 1 |
| APPLICATION NO. | : 17/051533 | |
| DATED | : October 29, 2024 | |
| INVENTOR(S) | : Anthony V. Torris et al. | |

It is certified that error appears in the above-identified patent and that said Letters Patent is hereby corrected as shown below:

On the Title Page

Item (57) Column 2, Line 1, delete "scaling" and insert -- sealing --

Item (57) Column 2, Line 12, delete "hi one embodiment," and insert -- in one embodiment, --

Signed and Sealed this
Thirty-first Day of December, 2024

Derrick Brent
*Acting Director of the United States Patent and Trademark Office*